(12) United States Patent
Kim et al.

(10) Patent No.: US 11,134,843 B2
(45) Date of Patent: Oct. 5, 2021

(54) APPARATUS AND METHOD OF MEASURING ELECTROCARDIOGRAM SIGNAL USING WIRELESS COMMUNICATIONS, AND COMPUTER-READABLE RECORDING MEDIUM

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Ji Hoon Lee, Gwangju (KR); Si Ho Shin, Gwangju (KR)

(73) Assignee: Industry-Academic Cooperation Foundation, Chosun University, Gwangju (KR)

(*) Notice: Subject to any disclaimer, the term of this patent is extended or adjusted under 35 U.S.C. 154(b) by 115 days.

(21) Appl. No.: 16/174,494

(22) Filed: Oct. 30, 2018

(65) Prior Publication Data
US 2020/0037876 A1    Feb. 6, 2020

(30) Foreign Application Priority Data
Aug. 1, 2018 (KR) .................. 10-2018-0089654

(51) Int. Cl.
*A61B 5/00* (2006.01)
*A61B 5/332* (2021.01)

(52) U.S. Cl.
CPC .......... *A61B 5/0006* (2013.01); *A61B 5/0024* (2013.01); *A61B 5/0028* (2013.01); *A61B 5/332* (2021.01); *A61B 5/681* (2013.01)

(58) Field of Classification Search
USPC .................................... 600/508–509
See application file for complete search history.

(56) References Cited

U.S. PATENT DOCUMENTS

| | | | |
|---|---|---|---|
| 2011/0009729 A1 | 1/2011 | Shin et al. | |
| 2012/0242501 A1* | 9/2012 | Tran ..................... | A61B 5/7465 340/870.02 |
| 2014/0100432 A1 | 4/2014 | Golda et al. | |
| 2017/0055862 A1 | 3/2017 | Youn et al. | |

FOREIGN PATENT DOCUMENTS

| | | |
|---|---|---|
| JP | 2008-017991 A | 1/2008 |
| JP | 2015-530225 A | 10/2015 |
| KR | 10-2011-0004660 A | 1/2011 |
| KR | 10-1651537 B1 | 8/2016 |
| KR | 10-2016-0110109 A | 9/2016 |
| KR | 102018007665 A | 12/2016 |
| KR | 1020180076655 A | 12/2016 |

* cited by examiner

*Primary Examiner* — Nicole F Lavert
(74) *Attorney, Agent, or Firm* — Renner, Otto, Boisselle & Sklar, LLP

(57) ABSTRACT

An apparatus for measurement of an electrocardiogram signal using wireless communications includes a submodule measuring a first signal by a heartbeat signal provided via a first electrode when a flag signal is wirelessly received, and a main module wirelessly transmitting the flag signal according to a predetermined sampling period, and measuring a second signal by a heartbeat signal provided through a second electrode. The main module is configured to synchronize a measurement time of the second signal with a measurement time of the first signal by measuring the second signal in consideration of a wireless transmission time of the flag signal.

12 Claims, 5 Drawing Sheets

APPARATUS AND METHOD OF MEASURING ELECTROCARDIOGRAM SIGNAL USING WIRELESS COMMUNICATIONS, AND COMPUTER-READABLE RECORDING MEDIUM

CROSS-REFERENCE TO RELATED APPLICATION(S)

This application claims benefit of priority to Korean Patent Application No. 10-2018-0089654 filed on Aug. 1, 2018 in the Korean Intellectual Property Office, the disclosure of which is incorporated herein by reference in its entirety.

BACKGROUND

1. Field

The present disclosure relates to an apparatus and a method of measuring an electrocardiogram signal, using wireless communications, and a computer-readable recording medium.

The present disclosure has been derived from a research undertaken as a part of a project [Project Number: S1601-20-1041, Project Title: Development of Brain-Body interface technology using AI-based multi-sensing], [Project Number: 1345330977, Project Title: User authentication technology based on wearable devices using multi-biosignal] to support the Research Projects by the Ministry of Science, ICT and Future Planning and the National IT Industry Promotion Agency, National Research Foundation of Korea.

2. Description of Related Art

In a method of measuring various-types of biological signals and the like, microelectrical signals generated in the body are detected, and the detected signals are expressed in graphs or as numerical values, thereby detecting abnormalities in body functions. In general, an electrode is attached to a measured body part, and electrical signals sensed by a module are received and processed through a wire, to be converted into values that may be confirmed by a user or a healthcare provider. Since electrical signals use a method of measuring a potential difference, based on the ground or a virtual ground, a plurality of electrodes are attached to the body, and the electrodes are physically connected to a single measurement module.

Biological signal measurements temporarily carried out at medical facilities may be used to measure anomalous signs that occur continuously. However, to measure signs that occur suddenly or only in certain situations, a method of determining whether a functional abnormality is present through all the recordings occurring in daily life may be used as users directly wear small-sized devices such as an ECG Holter monitor.

However, since such devices use physical wires, there is a disadvantage in that critical noise may be introduced into a signal due to the movement of a user or inconvenience may be caused in daily life of a user. While such devices are necessary for users who have been diagnosed with a disease or who have a functional abnormality, it may be difficult to use a universal and popular device due to the disadvantages above.

SUMMARY

An aspect of the present disclosure is to provide an apparatus and a method of measuring an electrocardiogram signal, using wireless communications, in which an electrocardiogram signal may be generated with the same level of performance as that of existing equipment without restricting the movement of a wearer while points in time measured in a main module and in a submodule may be synchronized, and a computer-readable recording medium.

According to an aspect of the present inventive concept, an apparatus for measurement of an electrocardiogram signal, using wireless communications, includes a submodule measuring a first signal by a heartbeat signal provided via a first electrode when a flag signal is wirelessly received; and a main module wirelessly transmitting the flag signal according to a predetermined sampling period, and measuring a second signal by a heartbeat signal provided through a second electrode. The main module is configured to synchronize a measurement time of the second signal with a measurement time of the first signal by measuring the second signal in consideration of a wireless transmission time of the flag signal.

According to an aspect of the present inventive concept, a method of measuring an electrocardiogram signal using wireless communications includes a first operation of measuring a first signal by a heartbeat signal through a first electrode, with a submodule, when a flag signal is wirelessly received; and a second operation of wirelessly transmitting the flag signal by a predetermined sampling period, and measuring a second signal by a heartbeat signal through a second electrode, with a main module. The second operation is performed to synchronize a measurement time point of the second signal with a measurement time point of the first signal, by measuring the second signal in consideration of a wireless transmission time of the flag signal.

According to an aspect of the present inventive concept, a computer-readable recording medium has a program recorded thereon to execute the method described above.

BRIEF DESCRIPTION OF DRAWINGS

The above and other aspects, features, and advantages of the present disclosure will be more clearly understood from the following detailed description, taken in conjunction with the accompanying drawings, in which.

DETAILED DESCRIPTION

Figure 1:
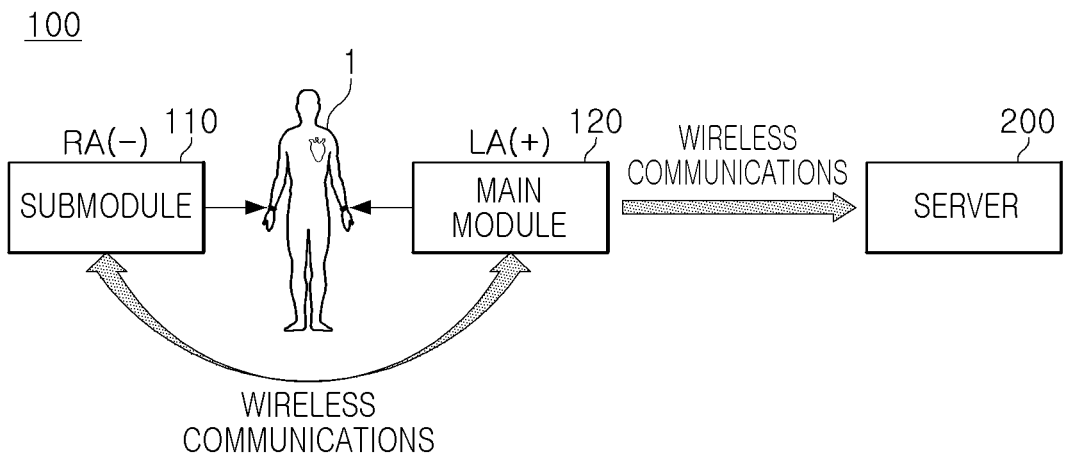
FIG. 1 is an overall schematic diagram of an apparatus for measurement of an electrocardiogram signal using wireless communications according to an exemplary embodiment in the present disclosure.

Hereinafter, embodiments in the present disclosure will be described with reference to the accompanying drawings. However, exemplary embodiments in the present disclosure may be variously modified, and the scope of the present invention is not limited to exemplary embodiments described below. The shape and size of elements in the drawings may be exaggerated for clarity, and elements denoted by the same reference numerals throughout the drawings are referred to the same elements.

FIG. 1 is an overall schematic diagram of an apparatus for measurement of an electrocardiogram signal using wireless communications according to an exemplary embodiment.

As illustrated in FIG. 1, an apparatus 100 for measurement of an electrocardiogram signal using wireless communications according to an exemplary embodiment may include a submodule 110 and a main module 120 attached to a human body and transmitting and receiving data through wireless communications. The main module 120 may be configured to transmit an electrocardiogram signal to an external server 200 through wireless communications. In this case, examples of the external server 200 may include a personal computer (PC), a smartphone, a tablet PC, and the like.

FIG. 1 shows the submodule 110 attached to a right arm RA of the human body 1 and the main module 120 attached to a left arm LA of the human body 1, respectively.

According to another exemplary embodiment, for example, when the submodule 110 is attached to either the left or right wrist or arm, the main module 120 may be attached to the other wrist or arm on the left or right side. Alternatively, when the submodule 110 is attached to either the left or right leg or ankle, the main module 120 may be attached to the other leg or ankle on the left or right side. The above-described attachment position is merely provided by way of example, and thus, various attachment positions may be provided.

The submodule 110 of the apparatus 100 for measurement of an electrocardiogram signal may be configured to measure a first signal based on a heartbeat signal through a first electrode when a flag signal is received wirelessly. The main module 120 of the apparatus 100 for measurement of an electrocardiogram signal may be configured to transmit the flag signal according to a predetermined sampling period wirelessly, and to measure a second signal based on a heartbeat signal through a second electrode, in detail, to measure the second signal in consideration of a wireless transmission time of the flag signal, thereby synchronizing points in time measuring the first and second signals.

Figure 2A:
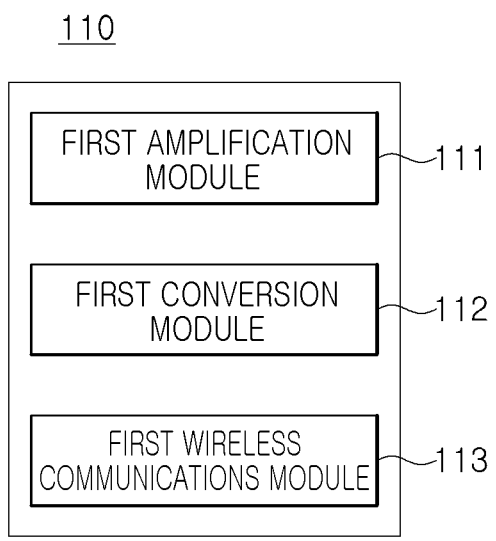
FIG. 2A is a block diagram illustrating the interior of a submodule in an apparatus for measurement of an electrocardiogram signal using wireless communications according to an exemplary embodiment in the present disclosure.
Figure 2B:
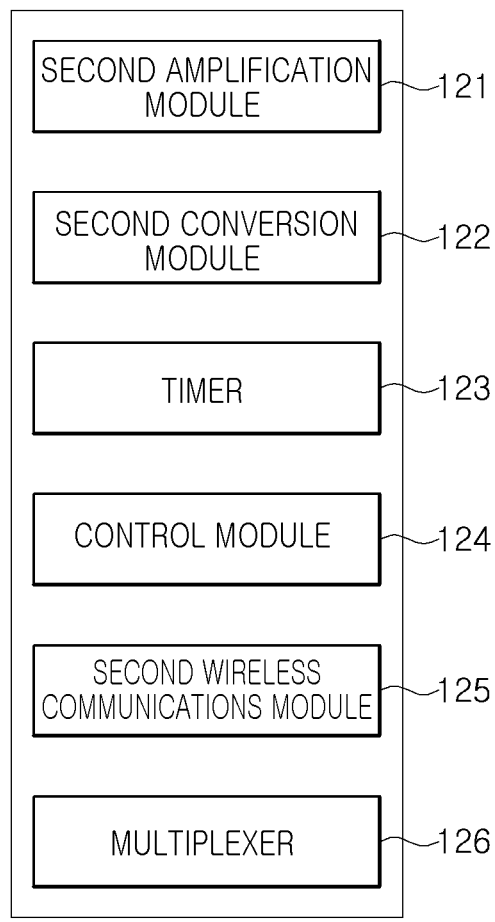
FIG. 2B is a block diagram illustrating the interior of a main module in an apparatus for measurement of an electrocardiogram signal using wireless communications according to an exemplary embodiment in the present disclosure.

In detail, FIG. 2A is a block diagram illustrating the interior of a submodule in an apparatus for measurement of an electrocardiogram signal using wireless communications according to an exemplary embodiment, and FIG. 2B is a block diagram illustrating the interior of a main module in an apparatus for measurement of an electrocardiogram signal using wireless communications according to an exemplary embodiment.

As illustrated in FIG. 2A, in an apparatus for measurement of an electrocardiogram signal using wireless communications according to an exemplary embodiment, the submodule 110 may include a first amplification module 111 amplifying a first signal input through a first electrode when a flag signal is wirelessly received, a first conversion module 112 converting the amplified first signal into a digital signal, and a first wireless communications module 113 wirelessly transmitting, the first signal converted into the digital signal, to the main module 120.

In addition, as illustrated in FIG. 2B, in the apparatus for measurement of an electrocardiogram signal using wireless communications according to an exemplary embodiment, the main module 120 may include a second amplification module 121 amplifying a second signal input through a second electrode, a second conversion module 122 converting the amplified second signal into a digital signal, a timer 123 counting a processing period of time from a point in time at which a flag signal is transmitted to a point in time at which the first signal having been converted into the digital signal is received from the submodule 110, and a control module 124 calculating an electrocardiogram signal from the second signal having been converted into the digital signal and from the first signal having been converted into the digital signal when the counted processing period of time is less than a predetermined sampling period, and initializing the main module 120 when the counted processing period of time is longer than the predetermined sampling period.

In detail, the second conversion module 122 may convert the amplified second signal into a digital signal at a point of time at which a predetermined first delay time D_A has elapsed from a point in time at which the flag signal is wirelessly transmitted.

In addition, the control module 124 may transmit the flag signal to the submodule 110, at a point in time at which a predetermined second delay time D_B has elapsed from the end of the processing period of time. In this case, the second delay time may be a value obtained by subtracting the processing period of time from the predetermined sampling period.

Further, the main module 120 in the apparatus for measurement of an electrocardiogram signal using wireless communications according to an exemplary embodiment may include a second wireless communications module 125 and a multiplexer 126.

In this case, the second wireless communications module 125 may wirelessly transmit the flag signal to the submodule 110 under the control of the control module 124, may wirelessly receive the first signal, an ADC result, measured by the submodule 110, and may transmit the measured electrocardiogram signal to the external server 200 (see FIG. 1) wirelessly.

Examples of the first wireless communications module 113 and the second wireless communications module 125 may include all-types of wireless communications modules such as a ZigBee module, a Bluetooth® module, a Wi-Fi module and the like.

The multiplexer 126 may be a device to select one of first signals measured by two or more submodules in the case in which the submodule 110 is provided as two or more submodules.

In addition, the apparatus for measurement of an electrocardiogram signal using wireless communications according to an exemplary embodiment may further include a right leg drive (RLD) module applying a predetermined voltage to a human body to amplify magnitudes of the first signal and the second signal.

Figure 3A:
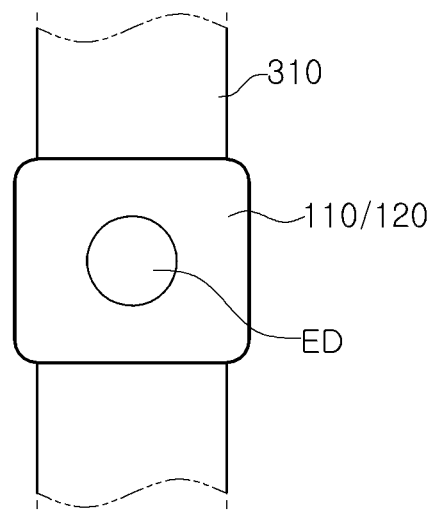
FIGS. 3A to 3C are views illustrating a main module and a submodule in an apparatus for measurement of an electrocardiogram signal using wireless communications according to exemplary embodiments in the present disclosure.
Figure 3B:
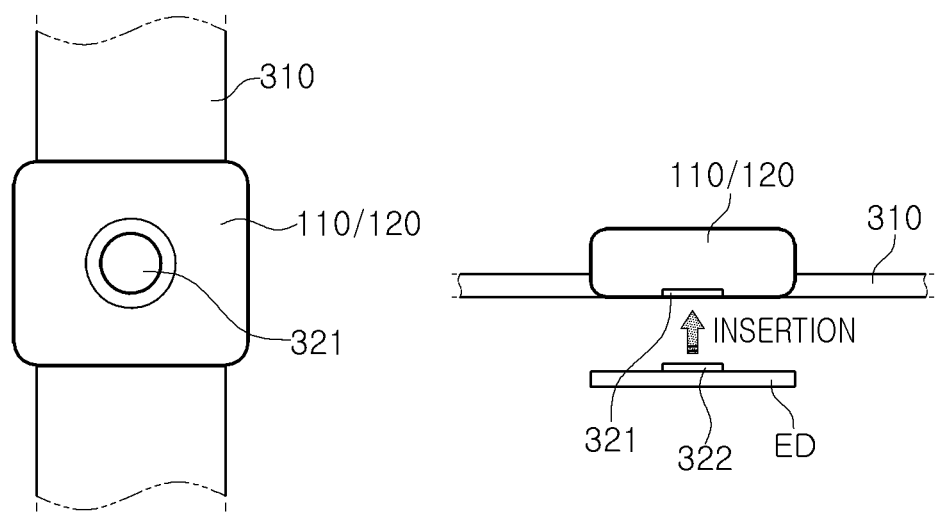
Figure 3C:
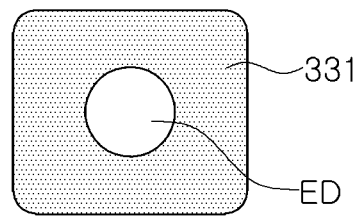

FIGS. 3A to 3C are views illustrating a main module and a submodule in an apparatus for measurement of an electrocardiogram signal using wireless communications according to exemplary embodiments.

As illustrated in FIG. 3A, the main module 120 or the submodule 110 may be coupled to a band 310, and a first electrode (referred to as ED) may be provided on one surface of a submodule 110 coupled to the band 310. Similarly, a second electrode ED may be provided on one surface of a main module 120 coupled to the band 310.

As illustrated in FIG. 3B, the main module 120 or the submodule 110 may be coupled to the band 310, and a first button-type connector 322 provided on the band ED and a detachable second button-type connector 321 may be provided on one surface of the main module 120 or the submodule 110.

In detail, the first button-type connector 322 may be provided on one surface of the first electrode ED, and on one surface of the submodule 110 facing thereto, the second button-type connector 321 may be provided to be detachable from the first button-type connector 322 of the first electrode ED, and the band 310 may be coupled to the submodule 110.

Similarly thereto, the first button-type connector 322 may be provided on one surface of the second electrode ED, and on one surface of the main module 120, the second button-type connector 321 may be provided to be detachable from the first button-type connector 322 of the second electrode ED, and the band 310 may be coupled to the main module 120.

On the other hand, a band-free form may be applied as illustrated in FIG. 3C.

In detail, an adhesive substance 331 may be provided under the submodule 110, and the first electrode ED may be provided on a portion of the submodule 110 on which the adhesive substance 331 is not provided. Similarly thereto, the adhesive substance 331 may be provided under the main module 120, and the second electrode ED may be provided on a portion of the main module 120 on which the adhesive substance 331 is not provided.

Figure 4:
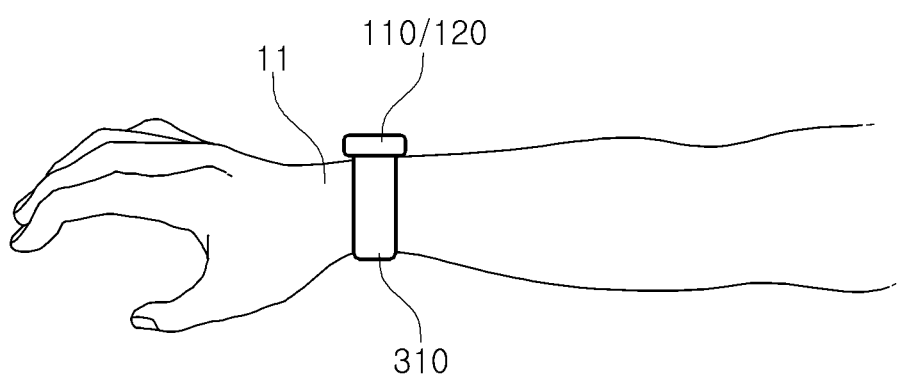
FIG. 4 is a diagram illustrating a state in which an apparatus for measurement of an electrocardiogram signal using wireless communications according to an exemplary embodiment in the present disclosure is worn.

FIG. 4 is a diagram illustrating a state in which an apparatus for measurement of an electrocardiogram signal using wireless communications according to an exemplary embodiment is worn.

In the band-type apparatus as illustrated in FIGS. 3A and 3B, it can be seen that the submodule 110 or the main module 120 may be easily attached to and detached from a wrist 11 of a human body by using the band 310.

As described above, according to an exemplary embodiment, since a measurement signal is transmitted between the main module and the submodule via wireless communications, rather than a physical wire, an electrocardiogram signal may be generated with the same level of performance as that of existing equipment without restricting the movement of a wearer. Further, since the signal is measured by the main module in consideration of a wireless transmission time of the flag signal transmitted to the submodule, points in time measured in the main module and the submodule may be synchronized.

Figure 5:
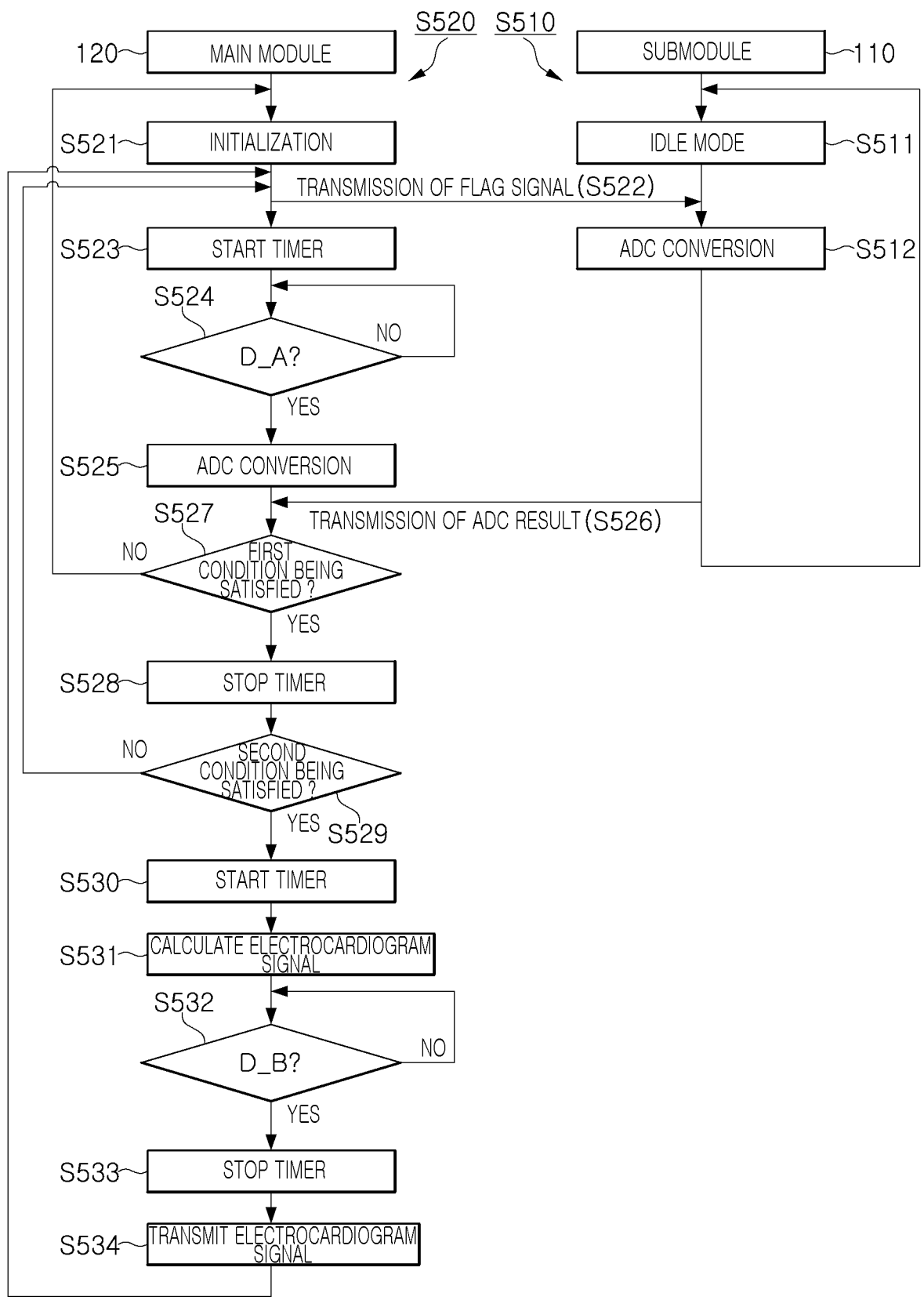
FIG. 5 is a flowchart illustrating a method of measuring an electrocardiogram signal using wireless communications according to an exemplary embodiment in the present disclosure.

FIG. 5 is a flowchart illustrating a method of measuring an electrocardiogram signal using wireless communications according to an exemplary embodiment.

Hereinafter, a method of measuring an electrocardiogram signal using wireless communications according to an exemplary embodiment will be described in detail with reference to FIGS. 1 to 5. However, to simplify the description, the description of the parts overlapping those described above with reference to FIGS. 1 to 4 will be omitted.

A method of measuring an electrocardiogram signal using wireless communications according to an exemplary embodiment may include a first operation S510 of measuring a first signal by a heartbeat signal through a first electrode, in the submodule 110, when a flag signal is wirelessly received, and a second operation S520 of wirelessly transmitting the flag signal by a predetermined sampling period and measuring a second signal by a heartbeat signal through a second electrode, in the main module 120.

In the second operation S520, as the second signal is measured in consideration of a wireless transmission time of the flag signal, a measurement time point of the second signal with a measurement time point of the first signal may be synchronized. In an exemplary embodiment of the present disclosure, the amplification of signals may be performed by the first and second amplification modules 111 and 121 in real time, and thus, the description thereof is omitted.

First, operations of the submodule 110 will be described. The submodule 110 may operate in an idle mode S511 before the flag signal is wirelessly received. When the flag signal is received from the main module 120 in S522, the submodule 110 may deviate from the idle module S511, and may convert the first signal by the heartbeat signal through the first electrode into a digital signal (referred to as an analog-to-digital conversion (ADC)) in S512.

When the ADC conversion is completed, the submodule 110 may wirelessly transmit an ADC result to the main module 120 in S526. The submodule 110 may then return to the idle mode S511.

Next, operations of the main module 120 will be described.

First, the main module 120 may be initialized in S521. When the initialization is completed, a flag signal may be transmitted to the submodule 110 in S522, and simultaneously therewith, an embedded timer 123 may be started in S523.

The time may be measured by the timer 123, and the control module 124 may continuously determine whether the measured time has reached a first delay time D_A in S524. For example, when the measured time reaches the first delay time D_A, the second conversion module 122 may convert the second signal by the heartbeat signal through the second electrode into a digital signal in S525. As such, the main module 120 may be provided with the control module to determine whether the measured time has reached the first delay time D_A, to synchronize the measurement time of the second signal with the measurement time of the first signal, in consideration of a wireless transmission time of the flag signal.

Next, the control module 124 may determine whether a first condition is satisfied in S527. In this case, the first condition indicates that the ADC conversion by the second conversion module 122 is completed and the ADC result is received from the submodule 110. When the first condition is satisfied, the timer 123 may be stopped in S528. When the first condition is not satisfied, the initialization operation S521 may be performed.

In operation S529, the control module 124 may determine whether a second condition is satisfied. The second condition is to determine whether a processing period of time is less than a predetermined sampling period in which the flag signal is transmitted. In this case, the processing period of time may be a period of time from the start of the timer to the end of the timer, for example, a period of time from a point in time at which the flag signal is transmitted to a point in time at which the first signal converted into a digital signal is received from the submodule 110.

As a result of the determination in operation S529, when the processing period of time is less than the predetermined sampling period, the second condition may be satisfied. Thus, the control module 124 may calculate an electrocardiogram signal from the second signal converted into the digital signal and the first signal converted into the digital signal.

In detail, the timer 123 may be started again in S530, and the control module 124 may calculate the electrocardiogram signal by obtaining a difference between the second signal converted into the digital signal and the first signal converted into the digital signal, in S531.

Thereafter, the control module 124 may determine whether the time counted by the timer 123 has reached a second delay time D_B in S532. When the time reaches the second delay time D_B, the control module 124 may stop the timer 123 in S533, and then, may wirelessly transmit the electrocardiogram signal to an external server (see 200 in FIG. 1) through a second wireless communications module 125, in S534. In this case, the second delay time D_B may be a value obtained by subtracting the processing period of time from the predetermined sampling period.

On the other hand, when the processing period of time is longer than the predetermined sampling period in the determination result in S529, the initializing operation S521 may be performed.

As described above, according to an exemplary embodiment, since a measurement signal is transmitted between the main module and the submodule via wireless communications, rather than a physical wire, the electrocardiogram signal may be generated with the same level of performance as that of existing equipment without restricting the movement of a wearer, and the signal may be measured in the main module in consideration of the wireless transmission time of the flag signal transmitted to the submodule. Thus, the points in time measured in the main module and the submodule may be synchronized.

The method of measuring an electrocardiogram signal using wireless communications according to an exemplary embodiment may be manufactured as a program to be executed by a computer, and may be stored in a computer-readable recording medium. Examples of the computer-readable recording medium may include a read only memory (ROM), a random access memory (RAM), a CD-ROM, a magnetic tape, a floppy disk, an optical data storage device, and the like. In addition, computer-readable recording media may be distributed in a network-connected computer system, in which computer-readable codes readable in a distributed manner may be stored and may be executed. Functional programs, codes, and code segments for implementations of the method may be easily carried out by programmers skilled in the art.

In addition, in describing an exemplary embodiment in the present disclosure, the term 'module' may be implemented in various ways, for example, by a processor, program instructions executed by a processor, a software module, a microcode, a computer program product, a logic circuit, an application-only integrated circuit, firmware, or the like.

As set forth above, according to an exemplary embodiment, since a measurement signal may be transmitted between a main module and a submodule via wireless communications, rather than a physical wire, an electrocardiogram signal may be generated with the same level of performance as that of existing equipment without limiting the movement of a wearer. In addition, since a signal may be measured in the main module in consideration of a wireless transmission time of a flag signal transmitted to a submodule, points in time measured in a main module and a submodule may be synchronized.

While exemplary embodiments have been shown and described above, it will be apparent to those skilled in the art that modifications and variations could be made without departing from the scope of the present invention as defined by the appended claims.

What is claimed is:

1. An apparatus for measurement of an electrocardiogram signal using wireless communications, comprising:
   a submodule attachable to a human body and configured to measure a first signal by a heartbeat provided via a first electrode when a flag signal is wirelessly received; and
   a main module attachable to the human body and configured to wirelessly transmit the flag signal according to a predetermined sampling period, and to measure a second signal by the heartbeat provided through a second electrode at a point in time at which a predetermined delay time for a wireless transmission of the flag signal has elapsed from a point in time at which the flag signal is transmitted to the submodule wirelessly, thus synchronizing a measurement time point of the second signal with a measurement time point of the first signal.

2. The apparatus of claim 1, wherein,
   the submodule is configured to include a first amplification module amplifying the first signal input through the first electrode when the flag signal is wirelessly received, a first conversion module converting the amplified first signal into a digital signal, and a first wireless communications module wirelessly transmitting the first signal converted into the digital signal to the main module, and
   the main module is configured to include a second amplification module amplifying the second signal input through the second electrode, and a second conversion module converting the amplified second signal into a digital signal.

3. The apparatus of claim 2, wherein the second conversion module is configured to convert the amplified second signal into a digital signal at a point in time at which a predetermined first delay time has elapsed from a point in time at which the flag signal is transmitted wirelessly.

4. The apparatus of claim 3, wherein the main module is configured to further include:
   a timer counting a processing period of time from a point in time at which the flag signal is transmitted to a point in time at which the first signal having been converted into the digital signal is received from the submodule, and
   a control module, calculating an electrocardiogram signal from the second signal having been converted into the digital signal and from the first signal having been converted into the digital signal when the counted processing period of time is less than the predetermined sampling period, and initializing the main module when the counted processing period of time is longer than the predetermined sampling period.

5. The apparatus of claim 4, wherein the control module transmits the flag signal to the submodule at a point in time at which a predetermined second delay time has elapsed from the end of the processing period of time, and the second delay time is a value obtained by subtracting the processing period of time from the predetermined sampling period.

6. The apparatus of claim 1, wherein, the first electrode is provided on one surface of the submodule coupled to a band, and the second electrode is provided on one surface of the main module coupled to a band.

7. The apparatus of claim 1, wherein, the first electrode is provided with a first button-type connector disposed on one surface thereof, the submodule is provided with a second button-type connector disposed on one surface thereof to be detachable from a connector of the first electrode, and the submodule is coupled to a band; and the second electrode is provided with a first button-type connector disposed on one surface thereof, the main module is provided with a second button-type connector disposed on one surface thereof to be detachable from a connector of the second electrode, and the main module is coupled to a band.

8. The apparatus of claim 1, wherein, the submodule is provided with an adhesive substance disposed thereunder, and the first electrode is provided on a portion of a surface of the submodule on which the adhesive substance is not provided; and the main module is provided with an adhesive substance disposed thereunder, and the second electrode is provided on a portion of a surface of the main module on which the adhesive substance is not provided.

9. The apparatus of claim 1, wherein the main module is configured to further include a multiplexer selecting one of first signals measured by two or more submodules when the submodule is provided as two or more.

10. The apparatus of claim 1, further comprising:

a right leg drive (RLD) module applying a predetermined voltage to a human body to amplify magnitudes of the first signal and the second signal.

11. A method of measuring an electrocardiogram signal using wireless communications, comprising:

a first operation of measuring a first signal by a heartbeat through a first electrode, with a submodule which is attached to a human body, when a flag signal is wirelessly received; and a second operation of wirelessly transmitting the flag signal by a predetermined sampling period, and measuring a second signal by the heartbeat through a second electrode, with a main module which is attached to the human body, at a point in time at which a predetermined delay time for a wireless transmission of the flag signal has elapsed from a point in time at which the flag signal is transmitted to the submodule wirelessly, thus synchronizing a measurement time point of the second signal with a measurement time point of the first signal.

12. A non-transitory computer-readable recording medium having a program recorded thereon to execute the method of claim 11.

* * * * *